United States Patent
Blair

(10) Patent No.: US 10,101,278 B2
(45) Date of Patent: Oct. 16, 2018

(54) PORTABLE SPECTROMETER FOR THE PRESUMPTIVE IDENTIFICATION OF ILLICIT DRUGS AND SUBSTANCES OF ABUSE

(71) Applicant: University of Central Florida Research Foundation, Inc., Orlando, FL (US)

(72) Inventor: Richard George Blair, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/889,318

(22) PCT Filed: May 9, 2014

(86) PCT No.: PCT/US2014/037483
§ 371 (c)(1),
(2) Date: Nov. 5, 2015

(87) PCT Pub. No.: WO2014/183026
PCT Pub. Date: Nov. 13, 2014

(65) Prior Publication Data
US 2016/0109371 A1     Apr. 21, 2016

Related U.S. Application Data

(60) Provisional application No. 61/821,472, filed on May 9, 2013.

(51) Int. Cl.
*G01N 21/77* (2006.01)
*G01N 21/64* (2006.01)
*G01N 21/25* (2006.01)

(52) U.S. Cl.
CPC .......... *G01N 21/77* (2013.01); *G01N 21/255* (2013.01); *G01N 21/645* (2013.01);
(Continued)

(58) Field of Classification Search
CPC ......... G01N 21/77; G01N 21/64; G01N 21/25
(Continued)

(56) References Cited

U.S. PATENT DOCUMENTS 3,834,903 A * 9/1974 Inoue .................. G03C 1/496
430/346
3,871,972 A * 3/1975 Sekine .................. B41M 5/20
205/53
(Continued)

FOREIGN PATENT DOCUMENTS

DE        2226994        12/1973

OTHER PUBLICATIONS

Hardt, H. D. et al, Zeitschrift für Analytische Chemie 1973, 265, 337-339.*
(Continued)

*Primary Examiner* — Arlen Soderquist
(74) *Attorney, Agent, or Firm* — Dunlap Codding, P.C.

(57) ABSTRACT

A portable spectrometer system is disclosed for more reliable and convenient on-site drug testing. More particularly, but not by way of limitation, the presently disclosed and/or claimed inventive concept(s) relates to a portable spectrometer system having a test strip having a fluorescent indicator, a fluorimeter, and a mobile computing device capable of determining the identity of an unknown substance in the sample.

24 Claims, 9 Drawing Sheets

(52) U.S. Cl.
CPC ........... *G01N 2021/7786* (2013.01); *G01N 2201/0221* (2013.01); *G01N 2201/061* (2013.01)

(58) Field of Classification Search
USPC ......... 422/400, 420, 425, 430, 82.05, 82.08; 436/46, 92, 98, 172; 356/218, 244, 317, 356/326, 328; 702/22, 30
See application file for complete search history.

(56) References Cited

U.S. PATENT DOCUMENTS

| | | | | | |
|---|---|---|---|---|---|
| 3,955,926 | A * | 5/1976 | Fischer | ............... | G01N 31/22 422/420 |
| 3,996,053 | A * | 12/1976 | Martin | ............... | G03C 1/725 430/374 |
| 4,337,065 | A * | 6/1982 | Hiratsuka | ............... | G01N 33/54386 422/423 |
| 4,668,359 | A * | 5/1987 | Postle | ............... | G01N 27/44747 106/205.71 |
| 4,833,088 | A * | 5/1989 | DeSimone | ............... | G01N 33/521 422/404 |
| 4,934,817 | A * | 6/1990 | Gassenhuber | ............... | G01N 33/92 356/244 |
| 5,073,629 | A * | 12/1991 | Dubler | ............... | G01N 33/533 436/536 |
| 5,158,849 | A * | 10/1992 | Katsen | ............... | C09D 5/24 430/58.1 |
| 5,212,099 | A * | 5/1993 | Marcus | ............... | G01N 21/1717 250/458.1 |
| 5,445,967 | A * | 8/1995 | Deuter | ............... | G06K 7/10851 235/462.25 |
| 5,526,120 | A * | 6/1996 | Jina | ............... | G01N 21/8483 356/244 |
| 6,159,424 | A * | 12/2000 | Kauhaniemi | ............... | A61B 5/150022 422/63 |
| 6,295,506 | B1 * | 9/2001 | Heinonen | ............... | A61B 5/14532 600/301 |
| 6,306,283 | B1 * | 10/2001 | Brandt | ............... | G01N 27/4166 205/775 |
| 7,267,799 | B1 * | 9/2007 | Borich | ............... | G01N 21/8483 235/462.11 |
| 7,283,245 | B2 * | 10/2007 | Xiao | ............... | G01N 21/253 356/434 |
| 7,420,663 | B2 * | 9/2008 | Wang | ............... | G01J 3/02 356/326 |
| 8,145,431 | B2 * | 3/2012 | Kloepfer | ............... | G01N 21/78 340/539.12 |
| 8,163,241 | B2 * | 4/2012 | Burke | ............... | G01N 21/645 204/400 |
| 8,367,013 | B2 * | 2/2013 | Kaylor | ............... | G01N 33/558 422/400 |
| 8,493,441 | B2 * | 7/2013 | Thonhauser | ............... | G01N 21/251 348/135 |
| 8,743,194 | B2 * | 6/2014 | Fletcher | ............... | G02B 21/0008 348/61 |
| 8,885,161 | B2 * | 11/2014 | Scheeline | ............... | G01J 3/42 356/328 |
| 8,889,424 | B2 * | 11/2014 | Ehrenkranz | ............... | G01N 33/78 422/425 |
| 8,916,390 | B2 * | 12/2014 | Ozcan | ............... | G01N 21/645 436/518 |
| 8,947,656 | B2 * | 2/2015 | Cunningham | ............... | G01J 3/28 356/300 |
| 9,023,295 | B2 * | 5/2015 | Chumanov | ............... | G01J 3/0291 422/561 |
| 9,057,702 | B2 * | 6/2015 | Ozcan | ............... | G01N 21/6486 |
| 9,241,663 | B2 * | 1/2016 | Jena | ............... | G01N 21/8483 |
| 9,244,066 | B2 * | 1/2016 | O'Driscoll | ............... | G01J 3/0202 |
| 9,445,749 | B2 * | 9/2016 | Erickson | ............... | G01N 33/52 |
| 9,489,703 | B2 * | 11/2016 | Kauniskangas | ............... | G06Q 50/22 |
| 2002/0058301 | A1 * | 5/2002 | Huh | ............... | C12Q 1/34 435/40.5 |
| 2003/0032077 | A1 * | 2/2003 | Itoh | ............... | A61B 5/0002 435/14 |
| 2003/0119202 | A1 * | 6/2003 | Kaylor | ............... | G01N 21/8483 436/514 |
| 2003/0151735 | A1 * | 8/2003 | Blumenfeld | ............... | G01N 21/6428 356/73 |
| 2005/0001144 | A1 * | 1/2005 | Cartlidge | ............... | G02B 21/0008 250/208.1 |
| 2005/0023439 | A1 * | 2/2005 | Cartlidge | ............... | G02B 27/0012 250/208.1 |
| 2005/0123439 | A1 * | 6/2005 | Patton | ............... | G01N 33/525 422/400 |
| 2005/0157304 | A1 * | 7/2005 | Xiao | ............... | G01N 21/253 356/446 |
| 2005/0201898 | A1 * | 9/2005 | Borich | ............... | G01N 21/78 422/82.05 |
| 2006/0222567 | A1 * | 10/2006 | Kloepfer | ............... | G01N 21/78 422/68.1 |
| 2006/0279732 | A1 | 12/2006 | Wang et al. | | |
| 2007/0275472 | A1 * | 11/2007 | Bertucci | ............... | G01N 21/78 436/80 |
| 2008/0088918 | A1 * | 4/2008 | O'Connell | ............... | G02B 21/365 359/371 |
| 2008/0101986 | A1 | 5/2008 | Saini et al. | | |
| 2009/0191092 | A1 * | 7/2009 | Burke | ............... | G01N 21/645 422/52 |
| 2010/0285610 | A1 * | 11/2010 | Saul | ............... | G01N 33/558 436/501 |
| 2011/0009163 | A1 | 1/2011 | Fletcher et al. | | |
| 2011/0053283 | A1 * | 3/2011 | Hood | ............... | G01N 33/14 436/104 |
| 2011/0054938 | A1 * | 3/2011 | Hood | ............... | G01N 33/14 705/3 |
| 2011/0063433 | A1 * | 3/2011 | Thonhauser | ............... | G01N 21/251 348/135 |
| 2012/0002852 | A1 * | 1/2012 | Karasikov | ............... | G06K 9/00127 382/128 |
| 2012/0157160 | A1 | 6/2012 | Ozcan et al. | | |
| 2012/0286046 | A1 * | 11/2012 | Ciurczak | ............... | G01J 3/0262 235/454 |
| 2012/0301528 | A1 * | 11/2012 | Uhlmann | ............... | A01N 59/16 424/405 |
| 2013/0093936 | A1 * | 4/2013 | Scheeline | ............... | G01J 3/42 348/345 |
| 2013/0157351 | A1 * | 6/2013 | Ozcan | ............... | G01N 21/6486 435/288.7 |
| 2013/0203043 | A1 * | 8/2013 | Ozcan | ............... | G06F 19/3487 435/5 |
| 2014/0002820 | A1 * | 1/2014 | Ko | ............... | G01J 3/0256 356/328 |
| 2014/0038222 | A1 * | 2/2014 | Alt | ............... | G01N 21/63 435/29 |
| 2014/0072189 | A1 * | 3/2014 | Jena | ............... | G01N 21/8483 382/128 |
| 2014/0154152 | A1 * | 6/2014 | Chumanov | ............... | G01J 3/0291 422/561 |
| 2014/0193839 | A1 * | 7/2014 | Cunningham | ............... | G01J 3/44 435/7.92 |
| 2014/0247340 | A1 * | 9/2014 | Kauniskangas | ............... | G06Q 50/22 348/92 |
| 2014/0296112 | A1 * | 10/2014 | O'Driscoll | ............... | G01J 3/0202 506/39 |
| 2014/0356978 | A1 * | 12/2014 | Jabour | ............... | G01N 33/54366 436/501 |
| 2015/0359458 | A1 * | 12/2015 | Erickson | ............... | G01N 33/52 455/557 |
| 2016/0077091 | A1 * | 3/2016 | Tyrrell | ............... | G01N 33/48792 436/501 |

OTHER PUBLICATIONS

Araki, H. et al, Inorganic Chemistry 2005, 44, 9667-9675.*
Crisp, S. et al, Analyst 1981, 106, 1318-1325.*
Abdel-Gawad, *Spectrophotometric determination of some pharmaceutical piperazine derivatives through charge-transfer and ion-*

(56) References Cited

OTHER PUBLICATIONS

*pair complexation reactions*, Journal of Pharmaceutical and Biomedical Analysis, 1997. 15(11): p. 1679-1685.

Andrew et al., *A Fluorescence Turn-On Mechanism to Detect High Explosives RDX and PETN.* J. Am. Chem. Soc., 2007. 129(23): p. 7254-7255.

Andryushechkin et al., *Epitaxial Growth of Semiconductor Films in the Interaction of Metals with Halogens. Atomic structure of CuI on Cu (110).* JETP Letters, 2006. 83(4): p. 162-166.

Argos et al., *The Crystal and Molecular Structure of 1-(1-Phenylcyclohexyl) Piperidine Hydrochloride.* Acta Cryst, 1970. B26: p. 53.

Barbieri et al., *Luminescent complexes beyond the platinum group: the d10 avenue.* Chem. Commun., 2008: p. 2185-2193.

Ciureanu et al., *A spectroscopic study of iodine complexes with aromatic amines.* Rev. Roum. Chim., 1979. 24(5): p. 655-61.

Cole, M., *Poison in party pills is too much to swallow*, Nature, 2011, 474, 253.

Cone et al., *Structure-activity relationship studies of phencyclidine derivatives in rats.* Journal of Pharmacology and Experimental Therapeutics, 1984. 228(1): p. 147-153.

Cooper et al., *A Note on the Crystal Structure of Marshite.* The Canadian Mineralogist, 1997. 35: p. 785-786.

Csaszar, *On the formation of aromatic secondary amine-iodine complexes.* ACH—Models Chem., 1995. 132(5): p. 845-51.

Csaszar, et al., *Formation and visible spectra of some molecular complexes of aliphatic and aromatic primary amines with iodine in chlorine-containing aliphatic solvents.* Acta Phys. Chem., 1990. 36(1-4): p. 66-82.

Ding, et al., *Geometry and Stability of $Cu_nN$ (n = 1-6) and $Cu_{3n}N_n$ (n = 1-5) Clusters.* J. Chem. Phys., 2009. 131: p. 174102.

Ford, et al., *Photoluminescence Properties of Multinuclear Copper(I) Compounds.* Chemical Reviews, 1999. 99(12): p. 3625-3648.

Hardt, et al., *Florescence thermochromism of pyridine copper iodides and copper iodide.* Zeitschrift f,r anorganische und allgemeine Chemie, 1973. 402(1): p. 107-112.

Hardt, et al., *Lumineszenzthermochromie, ein vergessenes Phänomen.* Naturwissenschaften, 1973. 61: p. 107-110, English language abstract.

Harvey et al., *Luminescent Coordination Polymers Built Upon $Cu_4X_4$ (X=Br,I) Clusters and Mono- and Dithioethers.* Macromolecular Rapid Communications, 2010. 31(9-10): p. 808-826.

Horváth, *Photochemistry of copper(I) complexes.* Coordination Chemistry Reviews, 1994. 135-136: p. 303-324.

Huffman et al., *Design, Synthesis and Pharmacology of Cannabimimetic Indoles.* Bioorganic & Medicinal Chemistry Letters, 1994. 4(4): p. 563-566.

Jiang, et al., *Crystal structure of tetra-m3-iodo-tetrakis[(nicotine)copper(I)], Cu4I4(C10H14N2)4* Z. Kristallogr. NCS, 2009. 224(3): p. 466-468.

Kitagawa, et al., *Flexibility of cubane-like $Cu_4I_4$ framework: temperature dependence of molecular structure and luminescence thermochromism of $[Cu_4I_4(PPh_3)_4]$ in two polymorphic crystalline states.* Chemical Communications, 2010. 46(34): p. 6302-6304.

Kunkely et al., *Luminescence detection and photodimerization of 1,3- dimethyluracil coordinated to copper(I).* Z. Naturforsch., B Chem. Sci., 2000. 55(5): p. 386-388.

Kurtal, *Spectroscopic and photochemical properties of d10 metal complexes.* Coordination Chemistry Reviews, 1990. 99: p. 213-252.

Kyle et al., *Photophysical studies in solution of the tetranuclear copper(I) clusters Cu4I4L4 (L = pyridine or substituted pyridine).* Journal of the American Chemical Society, 1991. 113(8): p. 2954-2965.

Lainton et al., *1-Alkyl-3-(1-naphthoyl)pyrroles: a new class of cannabinoid.* Tetrahedron Lett., 1995. 36(9): p. 1401-4.

Lim et al., *Copper(I) Cyanide Networks: Synthesis, Structure, and Luminescence Behavior. Part 2. Piperazine Ligands and Hexamethylenetrtramine(1).* Inorganic Chemistry, 2008. 47(15): p. 6931-6947.

Logan, et al., *3,4-methoxymethamphetamine (MDMA, Ecstasy) and driving impairment.* J Forens Sci, 2001. 46(6): p. 154-161.

Lopez-Delgado et al., *Fluorescence properties of methyl salicylate in vapor, liquid, and solution.* The Journal of Physical Chemistry, 1981. 85(7): p. 763-768.

Marcotrigiano et al., *Adducts of Piperidine, Piperazine, Methylpiperazine, and Morpholine with Bis(β-Ketoenolates) of Nickel(II).* Can. J. Chem., 1972. 50(16): p. 2557-2560.

Muñoz et al., *FTIR and fluorescence studies on the ground and excited state hydrogen-bonding interactions between 1-methylindole and water in water-triethylamine mixtures.* Chemical Physics, 2007. 335(1): p. 43-48.

O'Neal et al., *Validation of twelve chemical spot tests for the detection of drug abuse.* Forensic Science International, 2000, 109, 189-201.

Peat, *Analytical and Technical Aspects of Testing for Drug abuse: Confirmatory Procedures.* Clinical Chemistry, 1988, 34(3), 471-473.

Perera et al., *Recombination processes in dye-sensitized solid-state solar cells with CuI as the hole collector.* Solar Energy Materials and Solar Cells, 2003. 79(2): p. 249-255.

Rinde et al., *Colorimetric assay for aromatic amines.* Analytical Chemistry, 1976. 48(3): p. 542-544.

Rizk, et al., *Spectrophotometric Determination of Piperazine via Charge-transfer Complexes.* Analyst, 1981. 106: p. 1163-1167.

Samejima et al., *Condensation of ninhydrin with aldehydes and primary amines to yield highly fluorescent ternary products : I. Studies on the Mechanism of the Reaction and Some Characteristics of the Condensation Product.* Analytical Biochemistry, 1971. 42(1): p. 222-236.

Sayed et al., *Conductometric studies of charge transfer complexes of some alicyclic amines with iodine in solution.* Egypt. J. Chem., 2003. 46(4): p. 569-588.

Schieser, *Free radicals in alkaloidal color identification tests.* Journal of Pharmaceutical Sciences, 1964. 53(8): p. 909-913.

Skalski et al., *Ground state complexes between polar solvents and 1-methylindole: the origin of the Stokes' shift in their fluorescence spectra.* Chem. Phys. Lett., 1980. 70(3): p. 587-90.

Srivastava et al., *Charge transfer complexes of iodine with some donors by conductometric measurements.* Acta Cienc. Indica, [Ser.] Chem., 1980. 6(3): p. 142-4.

Swiatko, J.D.F., PR Zedeck, MS, *Further studies on spot tests and microcrystal tests for identification of cocaine* Journal of Forensic Sciences, 2003. 48(3): p. 1-5.

Tronic et al., *Copper(I) Cyanide Networks:‚Äâ Synthesis, Luminescence Behavior and Thermal Analysis. Part 1. Diimine Ligands.* Inorganic Chemistry, 2007. 46(21): p. 8897-8912.

Usdoj, *In The Matter of MDMA Scheduling.* Docket No. 84-48, 1984.

Vitale et al., *Origins of the Double Emission of the Tetranuclear Copper (I) Cluster $Cu_4I_4(pyridine)_4$: an ab Initio Study.* J. Phys. Chem., 1992. 96(21): p. 8203-8676.

Wada et al., *Simultaneous determination of N-benzylpiperazine and 1-(3-trifluoromethylphenyl)piperazine in rat plasma by HPLC-fluorescence detection and its application to monitoring of these drugs.* Biomedical Chromatography, 2011: p. n/a-n/a.

Yilmaz et al., *A novel two-dimensional silver(I) saccharinato coordination polymer constructed from weak AG . . . C interactions: Synthesis, IR spectra and X-ray structure.* Journal of Organometallic Chemistry, 2008. 693(26): p. 3885-3888.

You et al., *Synthesis of Deuterium Labeled Standards of 1-Benzylpiperazine, Fenetylline, Nicocodeine and Nicomorphine.* Journal of the Chinese Chemical Society, 2008. 55: p. 663-667.

Extremetech, http://www.extremetech.com/article2/0,2845,1156000,00.asp. 2010.

NCBI, *Phencyclidine—Compound Summary (CID 6468),* in http://pubchem.ncbi.nlm.nih.gov/summary/summary.cgi?cid=6468. 2011.

NCBI, *1-benzylpiperazine—Compound Summary (CID 75994)* in http://pubchem.ncbi.nlm.nih.gov/summary/summary.cgi?cid=75994&loc=ec_rcs. 2011.

Visioneer, http://www.visioneer.com/. 2010.

Drug Enforcement Administration, Drug & Chemical Evaluation Section, Jul. 2012.

(56) References Cited

OTHER PUBLICATIONS

Baoqiang et al., "*A simple strategy for pyridine visual sensing by the in-situ formation of tetranuclear copper iodine pyridine microcrystalline film on copper foil*", Thin Solid Films, Apr. 10, 2008, vol. 516, No. 21, pp. 7812-7815.

Ryu et al., "*Photoluminescence Properties of the Structurally Analogous Tetranuclear Copper(I) Clusters $Cu_4X_4(dump)_4$ (X = I, Br, Cl; dpmp = 2-(Diphenylmethyl)pyridine)*", Inorg. Chem., 1993, Issue 32, pp. 869-874.

Hardt, et al., Fluorescence thermochromism of copper(I) compounds. Naturwissenschaften, 1972. 59(8): p. 363.

Hardt, et al., Fluoreszenznachweis von Kupferionen und Kupfermetall. Naturwissenschaften, 1973. 60: p. 200-201.

Senkowski et al., Spectral study of the reaction between iodine and N,N-dimethylaniline in cyclohexane. J. Org. Chem., 1961. 26: p. 943-6.

Turkowski, Linker-induced anomalous emission of organic molecule-conjugated metal oxide nanoparticles. Science. In Submission.

Walker et al., Exciplex Studies. II. Indole and Indole Derivatives. J. Chem. Phys., 1967. 47(3): p. 1020-8.

Wing-Wah Yam et al., Luminescent polynuclear d10 metal complexes. Chemical Society Reviews, 1999. 28(5): p. 323-334.

Yamaguchi et al., Polymerization of formaldehyde with charge transfer complexes. Kobunshi Kagaku, 1971. 28 (312): p. 336-43.

Yang et al., Growth and Photoluminescence Characterization of Highly Oriented CuI/b-Cyclodextrin Hybrid Composite Film. Langmuir, 2005. 21(15): p. 6866-6871.

Yarosh et al., MDMA-like behavioral effects of N-substituted piperazines in the mouse. Pharmacology, Biochemistry and Behavior, 2007. 88(1): p. 18-27.

Lindbloom, http://www.brucelindbloom.com/index.html?ColorCalculator.html. 2009.

Stevens, Colour Tests. Isolation and Identification of Drugs, ed. E.G.C. Clarke. vol. 1. 1969, London: The Pharmaceutical Press.

Sayed, Charge transfer complexes of the interactions of iodine with some alicyclic amines. Egypt. J. Chem., 2003. 46 (2): p. 343-356.

Hunt, R.W.G. and M.R. Pointer, Appendix 8: Illuminant-Observer Weights for Calculating Tristimulus Values, in Measuring Colour. 2011, John Wiley & Sons, Ltd. p. 393-429.

Hunt, R.W.G. and M.R. Pointer, Obtaining Spectral Data and Tristimulus Values, in Measuring Colour. 2011, John Wiley & Sons, Ltd. p. 99-115.

Sayed, Charge transfer complexes of iodine interaction with some alicyclic amines. Mansoura Sci. Bull., A Chem., 2001. 28 (Suppl. 1): p. 87-98. abstract only.

Palenik, Microscopy and Microchemistry of Physical Science, in Forensic Identification of Controlled Substances. Forensic Science Handbook, ed. R. Saferstein. vol. 2. 1988, Englewood Cliffs, NJ: Prentice Hall.

\* cited by examiner

PORTABLE SPECTROMETER FOR THE PRESUMPTIVE IDENTIFICATION OF ILLICIT DRUGS AND SUBSTANCES OF ABUSE

CROSS-REFERENCE TO RELATED APPLICATIONS/INCORPORATION BY REFERENCE STATEMENT

This application is a national stage application filed under 35 USC 371 of PCT/US2014/037483, filed May 9, 2014; which claims benefit under 35 U.S.C. 119(e) of U.S. Provisional Patent Application Ser. No. 61/821,472, filed May 9, 2013, the entire contents of each of which are hereby expressly incorporated herein by reference.

STATEMENT REGARDING FEDERALLY SPONSORED RESEARCH OR DEVELOPMENT

A portion of this work was sponsored by National Institute of Justice Award Number 2012-R2-CX-K005. The U.S. Government therefore has certain rights in the invention.

BACKGROUND

The problem faced by the drug analysts in the forensics community is the difficulty in identifying certain types of controlled substances. The frequency of new drugs introduced in the party environment is at an alarming rate and this enhances the problem faced by the drug analysts. One such drug hard to identify is benzylpiperazine (BZP), commonly known as Legal X. Currently, there are no presumptive tests available for BZP. Additionally, phenylcyclidine (PCP) and cocaine cannot be distinguished from each other using the conventional presumptive methods. Problems like these can lead to false positives or negatives for a certain drug because of the indistinguishable presumptive results.

There are many reagent kits that exist which are used to presumptively identify the drugs based on the color they yield. Different tests are used to identify certain drugs. For example, Marquis' reagent, a solution of formaldehyde and sulfuric acid, is used to identify MDMA (ecstasy) and some other opiates while a cobalt thiocyanate test is used to detect the presence of cocaine. These reagents are added to an unknown drug and react with it to result in a change of color. The resulting color will correspond to a specific drug. The problem that presents itself is that the results depend on the perception of color by the officers or agents using the kits and their ability to compare the result to those in a given list of drugs and their resultant color. In addition, some of the results give a range of colors (i.e. "strong reddish orange to deep reddish brown" or "olive green to yellow"), which make it even more difficult for a consensus presumption of the identity of the drug. In short, this method has a relatively high rate of false positives and false negatives. In the case of the cobalt thiocyanate test, diphenhydramine (e.g., Benadryl®, available from McNeil Consumer Healthcare, Fort Washington, Pa.) yields results similar to cocaine. Confirmatory testing of these unknown substances can be done by methods such as TLC and GC-MS. However, these methods are time consuming as most of the GC-MS samples are done in situ. Portable GC-MS devices do exist, but the major drawback is that they need properly trained officers or agents to use them and the equipment is expensive.

The idea of an easy-to-use, low cost and portable device to identify unknown drugs is very attractive in the forensics community. Thus, there is a need for a low cost and portable device that can presumptively identify illicit drugs and common substances of abuse. It is to such a low cost and portable device that the present disclosure is directed.

BRIEF DESCRIPTION OF THE SEVERAL VIEWS OF THE DRAWINGS

The accompanying drawings, which are incorporated in and constitute a part of this specification, illustrate one or more implementations described herein and, together with the description, explain these implementations. In the drawings.

DETAILED DESCRIPTION OF THE PRESENTLY DISCLOSED AND CLAIMED INVENTION

Figure 1:
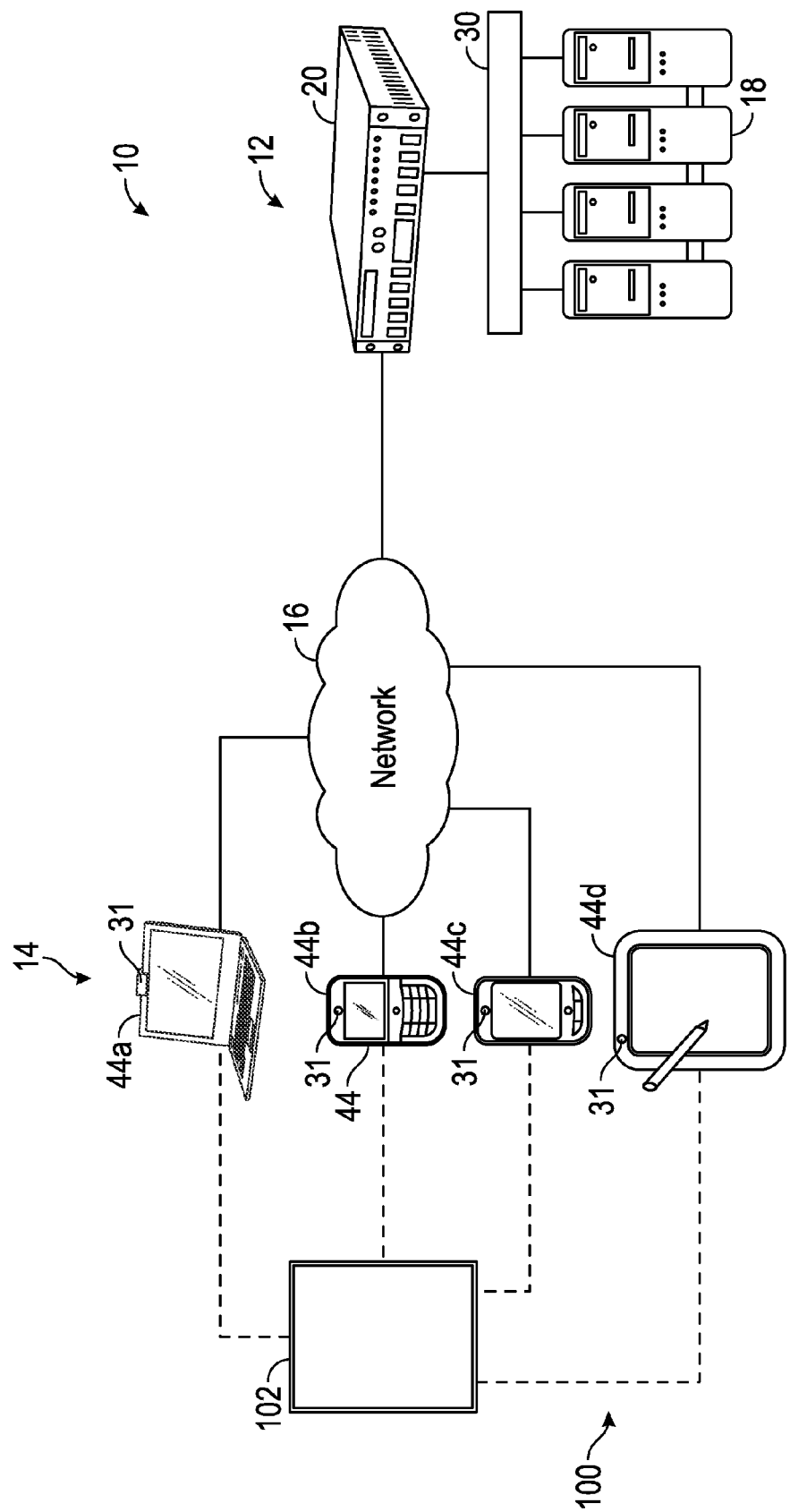
FIG. 1 is a schematic diagram of hardware forming an exemplary embodiment of a portable spectrometer system constructed in accordance with the present invention for analyzing an emission to determine an identity of an unknown substance.

Before explaining at least one embodiment of the invention in detail, it is to be understood that the invention is not limited in its application to the details of construction, experiments, exemplary data, and/or the arrangement of the components set forth in the following description or illustrated in the drawings.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

In one embodiment, the present disclosure describes a portable spectrometer system that includes a camera of a smart phone to obtain an emission spectrum of an unknown sample. Copper(I) iodide and other $d^{10}$ metal salts can be used to form luminescent cluster compounds with amines, such as alkaloids and opiates, that can be used to identify unknown substances on the fly. When $d^{10}$ metals are in solution with an amine present, a polynuclear cluster compound is formed. CuI is known to form a $Cu_4I_4L_4$, in which L is a ligand coordinated to the copper via its nitrogen (for amines) or phosphorus (for phosphines). (See, e.g., Ryu, C. K., et al., Iorg. Chem., 1993, 32, 869-874). For the purpose of directly testing an unknown substance, CuI can be used to test for amines in the form of alkaloids, opiates, and other drugs that have amine groups.

The $d^{10}$ metal salt can be a compound comprising a metal with an electronic configuration of $d^{10}$ and an anion selected from the group consisting of group 17 elements (i.e., halogens), cyanide (CN), thiocyanate (SCN), and combinations thereof. In one embodiment, the $d^{10}$ metal salt can be selected from the group consisting of copper (I) iodide, copper (I) bromide, silver (I) iodide, silver (I) bromide, gold (I) bromide, gold (I) iodide, zinc iodide, zinc bromide, cadmium iodide, cadmium bromide, mercury (I) iodide, mercury (I) bromide, and combinations thereof. Further, when referring to a $d^{10}$ metal it is meant any metal whose ten outer most electrons are in the orbitals such that the electron configuration is $d^{10}$.

In one non-limiting embodiment, an unknown sample is applied to a test strip (piece of filter paper coated with, for example but without limitation, CuI) forming a cluster compound that emits luminescence under UV radiation. In this embodiment, the portable spectrometer system uses an LED excitation source that emits at 254 nm. A smart phone application is stored within a non-transitory computer readable medium, such as memory within the smart phone. The smart phone application can be executed by one or more processors of the smart phone to analyze the luminescence emission of the resulting cluster compound on the test strip and ultimately obtain the emission spectrum of the sample. The portable spectrometer system may also include a library database that contains the spectral information for common drugs. By comparing the emission spectrum of the sample (as preferably represented by pixel values within an image) with the entries in the library database, the identification of the unknown sample can be rapidly determined on-site. The library database can be stored on the smart phone, or hosted remotely by a remote host system that the smart phone accesses via a wireless network. Although disclosed as a piece of filter paper in the above-recited embodiment, the test strip can be any substrate that does not fluoresce when subjected to short and long wave ultraviolet radiation.

In another embodiment, the test strip comprises a $d^{10}$ metal salt as described above and a polymer selected from the group consisting of polyvinylpyrrolidone, polyvinyl alcohol, and combinations thereof. It has been found that the combination of a $d^{10}$ metal salt and a polymer like, for example, polyvinylpyrrolidone, can form a film and/or coating on a substrate that produces good emission spectrums and has the consistency of a paint-like composition prior to drying. The test strip comprising the above-described $d^{10}$ metal salt and polymer selected from the group consisting of polyvinylpyrrolidone, polyvinyl alcohol, and combinations thereof can be formed by adding the above-described $d^{10}$ salt to an aqueous solution comprising the above-described polymer and allowing the solution to dry. In one embodiment, the test strip comprising the above-described $d^{10}$ metal salt and polymer selected from the group consisting of polyvinylpyrrolidone, polyvinyl alcohol, and combinations thereof can be a film independent of a substrate. In another embodiment, the test strip comprising the above-described $d^{10}$ metal salt and polymer selected from the group consisting of polyvinylpyrrolidone, polyvinyl alcohol, and combinations thereof can be a coating on a substrate.

Referring now to the drawings, and in particular to FIG. 1, shown therein and designated by a reference numeral 10 is an exemplary portable spectrometer system constructed in accordance with the present invention.

Preferably, the portable spectrometer system 10 is distributed, and includes a host system 12, communicating with one or more user devices 14 via a network 16. The network 16 can be the Internet or other network. In either case, the host system 12 typically includes one or more servers 18 configured to communicate with the network 16 via one or more gateways 20. When the network 16 is the Internet, the primary user interface of the portable spectrometer system 10 is delivered through a series of web pages, but the primary user interface can be replaced by another type of interface, such as a Windows-based application, or a mobile device application (hereafter referred to as an "App").

The network 16 can be almost any type of network although Internet and Internet 2 networks are preferred because of the wide support of their underlying technologies. The preferred embodiment of the network 16 exists in an Internet environment, which means a TCP/IP-based network. It is conceivable that in the near future, the preferred or other embodiments may wish to use more advanced networking topologies.

The servers 18 can be networked with a LAN 30. The gateway 20 is an entity responsible for providing access between the LAN 30 and the network 16. The gateway 20 can also be used as a security means to protect the LAN 30 from attack from external networks such as the network 16.

The LAN 30 network can be based on a TCP/IP network such as the Internet, or it can be based on another underlying network transport technology. The preferred embodiment uses an Ethernet network with TCP/IP because of the availability and acceptance of underlying technologies, but other embodiments may use other types of networks such as Fibre Channel, SCSI, Gigabit Ethernet, etc.

As discussed above, in one preferred embodiment, the host system 12 includes the servers 18. The configuration of the server hardware will depend greatly upon the requirements and needs of the particular embodiment of the portable spectrometer system 10. Typical embodiments, including the preferred embodiment, will include multiple servers 18 with load balancing to increase stability and availability.

It is envisioned that the servers 18 will include database servers and application/web servers. The database servers are preferably separated from the application/web servers to improve availability and also to provide the database servers with improved hardware and storage.

The user devices 14 can be any number and type of devices comprising an optical sensor 31, such as a camera, and a processor (not shown). The user devices 14 can be implemented as a portable device such as a mobile computing device 44 (for example, illustrated as 44a through 44d in FIG. 1). Nonexclusive examples of mobile computing device 44 include a laptop computer 44a (or handheld computer); a cellular telephone 44b such as a "smart phone" with a micro or embedded Web Browser; a Portable Digital Assistant 44c (PDA) capable of wireless network access; a pen-based or tablet computer 44d. Current embodiments of portable spectrometer system 10 can also be modified to use any of these or future developed devices.

In another example, the user device 14 may involve a user, using a computer with a display, keyboard, and mouse. The user device 14 may use a type of software called a "browser" to render HTML/XHTML content that is generated when requesting resources from a source, such as the host system 12. In the preferred embodiment, the portable spectrometer system 10 is designed to be compatible with major Web Browser vendors (for example, Microsoft Internet Explorer, Netscape Navigator, and Opera). Other embodiments may wish to focus on one particular browser depending upon the common user base using the portable spectrometer system 10.

The portable spectrometer system 10 is designed in this way as to provide flexibility in its deployment. Depending upon the requirements of the particular embodiment, the portable spectrometer system 10 could be designed to work in almost any environment such as a desktop application, a web application, or even simply as a series of web services designed to communicate with an external application.

Although some specifics for software and hardware components may be mentioned herein, it will be understood that a wide array of different components could be substituted, such as using different database vendors or even replacing the databases with XML-based document stores.

When the portable spectrometer system 10 is used to execute the logic of the processes described herein, such computer(s) and/or execution can be conducted at a same geographic location or multiple different geographic locations. Furthermore, the execution of the logic can be conducted continuously or at multiple discrete times.

The portable spectrometer system 10 includes one or more computer readable medium adapted to store instructions and/or data. The computer readable medium can be a part of the host system 12, the user devices 14 or combinations thereof.

Figure 2:
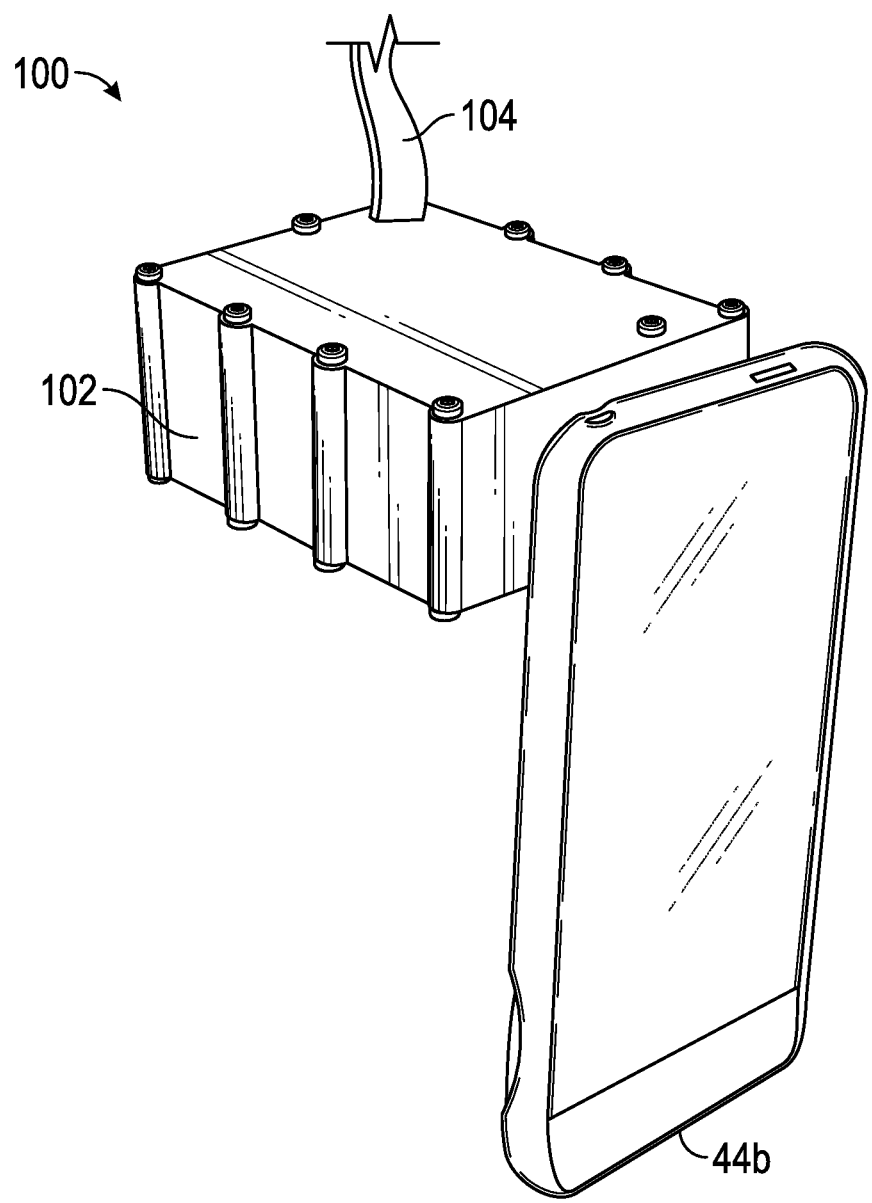
FIG. 2 is a pictorial representation of a mobile computing device, for example, a cellular telephone, and a fluorimeter of the portable spectrometer system generating and collecting an emission spectrum of a test strip with an unknown substance in accordance with the present invention.

The portable spectrometer system 10 includes one or more portable spectrometers 100 comprising a fluorimeter 102 working in conjunction with the mobile computing device 44 (illustrated, for example, as 44a-44d in FIG. 1) to analyze an unknown substance on a test strip 104 (not shown in FIG. 1). FIG. 2 is a pictorial representation of an exemplary portable spectrometer 100 with an exemplary mobile computing device, for example, a cellular telephone 44b, and fluorimeter 102 generating and collecting an emission spectrum of a test strip 104 with an unknown substance in accordance with the present disclosure. It should be recognized by a person of ordinary skill in the art that the mobile computing device should not be limited to a cellular telephone and instead can apply to any mobile computing device comprising an optical sensor 31 and a processor, e.g., a laptop computer 44a, PDA 44c, or a tablet computer 44d as illustrated in FIG. 1.

Figure 3:
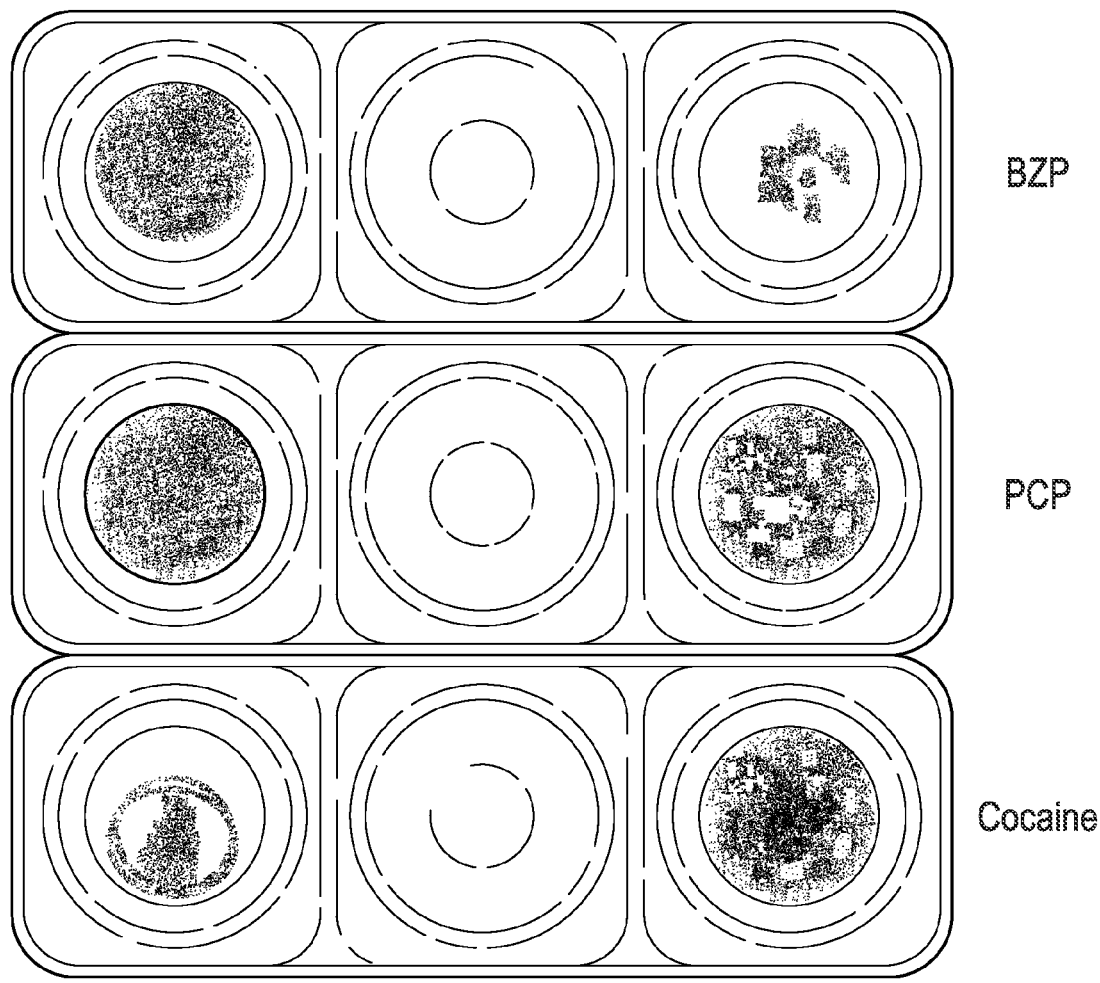
FIG. 3 is a photograph of emissions caused by different substances with a luminescent cluster compound being stimulated by UV radiation in accordance with the presently disclosed inventive concepts.

The test strip 104 may have a fluorescent indicator and be adapted to receive a sample of the unknown substance. When $d^{10}$ metals are in solution with an amine present, a polynuclear cluster compound is formed. CuI is known to form a $Cu_4I_4L_4$, in which L is a ligand coordinated to the copper via its nitrogen (for amines) or phosphorus (for phosphines). For the purpose of directly testing an unknown substance, the CuI may be utilized to test for amines in the form of alkaloids, opiates, and other drugs that have amine groups. For example, FIG. 3 is a photograph of emissions caused by different substances with a luminescent cluster compound being stimulated by UV radiation in accordance with the presently disclosed inventive concepts. An unknown sample is applied to the test strip 104 (for example, a piece of filter paper coated with CuI) forming a cluster compound that emits luminescence under UV radiation.

In an exemplary embodiment, the test strips 104 may be made with Whatman filter paper. The paper may be cut into 1 cm wide×2 cm long strips, for example, or in any size so as to fit into the fluorimeter 102 of the portable spectrometer 100. In one embodiment, a saturated solution of copper(I) iodide in acetonitrile is made and the strips of filter paper are dipped into the solution and then dried, wherein the acetonitrile evaporates. This process coats the test strips 104 with layers of CuI crystal on the surface. The coating for copper (I) iodide, as disclosed in the above-recited embodiment, and for any of the above-described $d^{10}$ metal salts has a thickness in a range from about 1 μm to about 1 mm. Additionally, although acetonitrile is disclosed in this particular embodiment, the solvent can comprise any weakly coordinating nitrogen-containing solvent including, for example but without limitation, amides, nitriles, and combinations thereof. With the CuI on the filter paper, the test strips 104 are ready to detect the amines. The sample of the unknown substance can be applied to the test strips 104 in different ways. One way is to simply apply the unknown substance, whether solid or liquid, onto the test strip 104 and then add a drop of solvent, such as acetonitrile. The solvent, as recited above, can comprise any weakly coordinating nitrogen-containing solvent. For example, but without limitation, the solvent can comprise a solvent selected from the group consisting of amides, nitriles, and combinations thereof. Or more specifically, the solvent can comprise for example but without limitation, acetonitrile, formamide, or combinations thereof. The addition of the solvent allows for cluster formation on the surface of the test strip 104. Another way the substance can be applied is to make a saturated solution of the substance in the solvent acetonitrile then dip the test strip 104 in the solution in the same manner as when the test strips 104 are dipped in the CuI. The latter method tends to give a more consistent coating of the cluster of the substance with CuI on both sides of the test strip 104 as opposed to the former method, which will only have the luminescent cluster compound present on the area of the test strip 104 the substance was applied to. The test strip 104 may be allowed to dry and then placed in the fluorimeter 102 of the portable spectrometer 100 to be analyzed.

Figure 4:
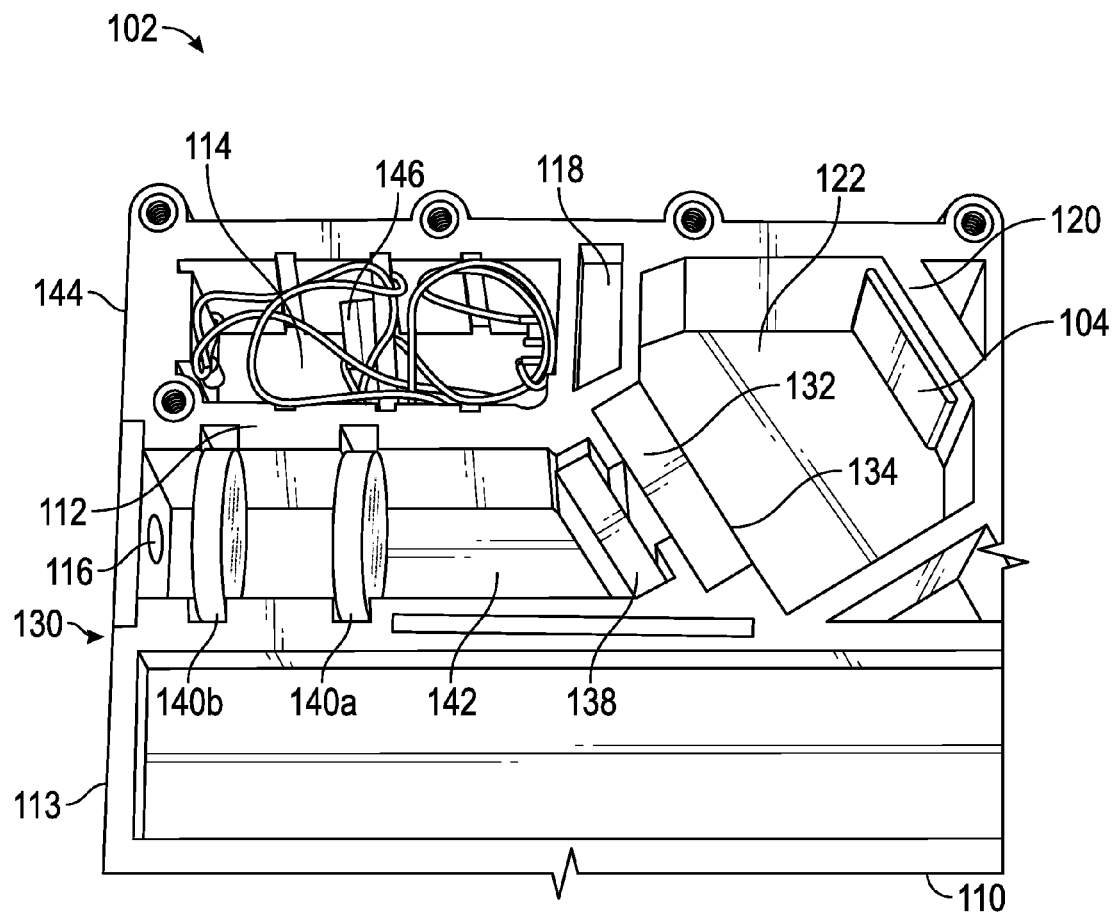
FIG. 4 is a pictorial representation of a part of a fluorimeter constructed in accordance with the presently disclosed inventive concepts.

FIG. 4 is a pictorial representation of a part of a fluorimeter 102 constructed in accordance with the presently disclosed inventive concepts. The fluorimeter 102 comprises a housing 110 having a plurality of interconnected walls 112 at least partially surrounding a cavity 114, where at least one of the walls 113 has an opening 116. In one embodiment, the housing 110 is of a small size such that the fluorimeter 102 is easily portable. In a nonexclusive example, the housing 110 has outer dimensions of 7.0 cm length, by 5.3 cm width, by 3.2 cm height. The interconnected walls 112 are preferably made of a material that is opaque to ambient light, and also preferably completely surround the cavity 114 so as to prevent the occurrence of unwanted light from interfering with the sample or adding noise to the emission spectrum generated by the fluorimeter 102. The fluorimeter 102 also includes a light source 118 positioned in the cavity 114 and adapted to emit light having a path. In one embodiment, the light source 118 is a light emitting diode (LED) excitation source that emits at 254 nm. A power source (not shown), such as one or more batteries, may also be included in the housing 110 for providing electrical power to the light source 118 as well as other electronic circuitry utilized to drive the light source 118. The housing 110 can be constructed using any suitable technique, such as three-dimensional printing.

The fluorimeter 102 also includes a support 120 for receiving the test strip 104 having the sample to be analyzed. The support 120 may be located within the path of the light such that the light contacts the sample to cause an emission from the fluorescent indicator on the test strip 104 in combination with the sample. The support 120 may be located within a reaction cavity 122 of the housing 110.

The fluorimeter 102 may also include an optical spectrum separation assembly 130 positioned to receive the emission from the fluorescent indicator located at the support 120 in the reaction cavity, separate the emission into an emission spectrum, and direct the separated emission spectrum through the opening 116. In one embodiment, the spectrum separation assembly 130 may include an optical guide 132 within the cavity 114 in the path of the light and constructed of a material that is opaque to the light. The optical guide 132 may have a slit, e.g., an air slit 134 in the path of the light that passes a portion of the light.

Figure 5:
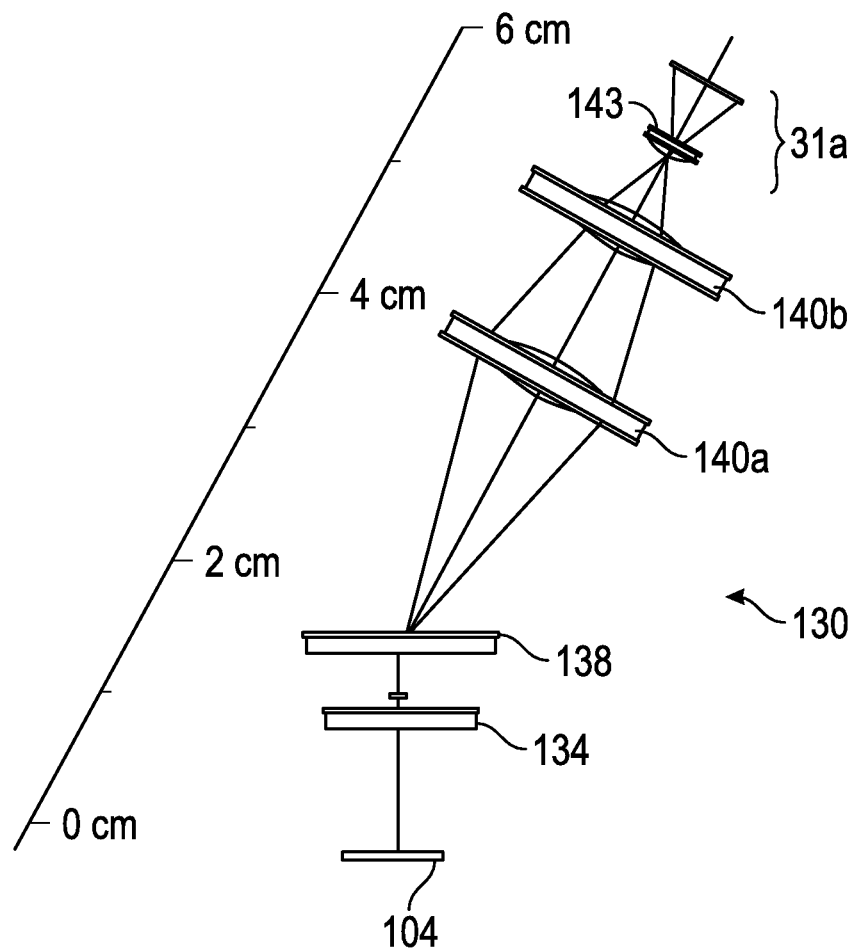
FIG. 5 is a diagrammatic representation of a path through which an emission is separated into its emission spectra and guided to an optical sensor in accordance with the presently disclosed inventive concepts.

In one embodiment, the optical spectrum separation assembly 130 comprises one or more diffraction grating 138 in the path of the light following the optical guide 132. The spectrum separation assembly 130 may also include one or more lenses 140 (illustrated, for example, as 140a and 140b in FIGS. 4-6) located in an emission channel 142. For example, FIG. 5 is a diagrammatic representation of an exemplary path and spectrum separation assembly 130 through which an emission is separated into its emission spectra and guided to an optical sensor 31a in accordance with the presently disclosed inventive concepts. In FIG. 5, the luminescence emitted from the test strip 104 travels through the air slit 134 then through the diffraction grating 138 which diffracts the light through a first lens 140a and a second lens 140b and then to an optical lens 143 of the optical sensor 31a of the mobile computing device 44 (illustrated, for example, in FIG. 1 as 44a-44d and as 44b in FIG. 2) that focuses the luminescence onto the optical sensor 31a.

Returning now to FIG. 4, in one embodiment, the fluorimeter 102 may also include a switch 144 located on a wall 112, for example in one embodiment wall 113, for sensing a presence of the mobile computing device 44 on the wall 112. The switch 144 may be operably connected to the light source 118 for enabling the light source 118 to emit light responsive to the presence of the mobile computing device 44 on the wall 112. The switch 144 may be operably connected to the light source 118 with a circuit 146. As stated above, It should be recognized by a person of ordinary skill in the art that the mobile computing device should not be limited to a cellular telephone and instead can apply to any mobile computing device comprising an optical sensor 31 and a processor, e.g., a laptop computer 44a, PDA 44c, or a tablet computer 44d as illustrated in FIG. 1.

Figure 6:
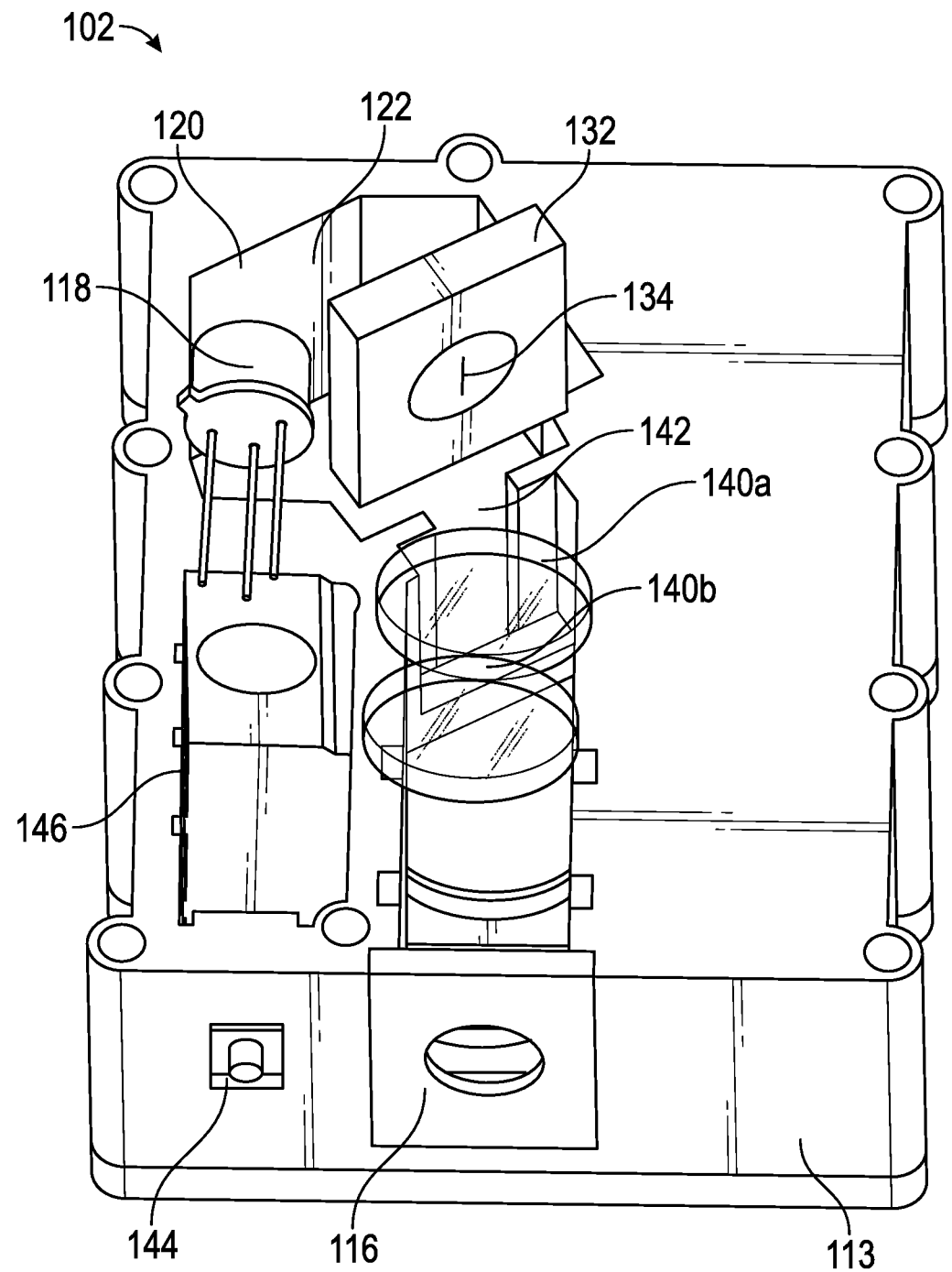
FIG. 6 is a diagrammatic representation of a partially exploded view of the components forming the fluorimeter in accordance with the presently disclosed inventive concepts.

FIG. 6 is a diagrammatic representation of a partially exploded view of the components forming the fluorimeter 102 in accordance with the presently disclosed inventive concepts. In the exemplary embodiment shown, the light source 118 is an LED capable of emitting at 254 nm, which is enabled and disabled via the circuit 146 connected to the switch 144 in the wall 113. Enabling the light source 118 causes the light source 118 to irradiate light, for example, light of 254 nm, onto the test strip 104 (not shown in FIG. 6) on the support 120 in the reaction cavity 122. The substance on the test strip 104 (not shown in FIG. 6) emits luminescence of a certain range of wavelengths, depending on the identity and nature of the substance. Here, the emitting luminescence then passes through an optical guide 132 and air slit 134 and a diffraction grating 138 (not shown in FIG. 6) then through two lenses 140a, 140b via the emission channel 142 to reach the opening 116 (exit window) in the wall 113.

Referring back to FIG. 2 and the spectrometer 100 shown therein in view of the illustrations depicted in FIGS. 4 and 6, the mobile computing device 44 (e.g., illustrated as a cellular telephone 44b in FIG. 2) may be positioned adjacent to the fluorimeter 102 such that the optical sensor 31, such as a camera, of the mobile computing device 44 is aligned with the opening 116 in the wall 113 of the fluorimeter 102. Pressing the mobile computing device against the switch 144 in the wall 113 of the fluorimeter 102 activates the switch 144 to cause the light source 118 to irradiate light. The camera of the mobile computing device 44 may act as a detector for the portable spectrometer 100, forming an image from the light emitted from the fluorimeter 102. The processor of the mobile computing device 44 may execute instructions to analyze the image to determine an identity of the unknown substance by comparing pixel values representative of emission spectra within the image to a library of emission spectra of known substances. Again, a person of ordinary skill in the art will recognize that the mobile computing device should not be limited to a cellular telephone and instead can apply to any mobile computing device comprising an optical sensor 31 and a processor, e.g., a laptop computer 44a, PDA 44c, or a tablet computer 44d as illustrated in FIG. 1.

The instructions may be in the form of software such as a smart phone application. The library of emission spectra may be stored within the mobile computing device 44 (illustrated as 44a-44d in FIGS. 1 and 44b in FIG. 2)_and/or stored remotely, such as in the remote servers 18, and accessed via the network 16 of the portable spectrometer system 10.

Figure 7:
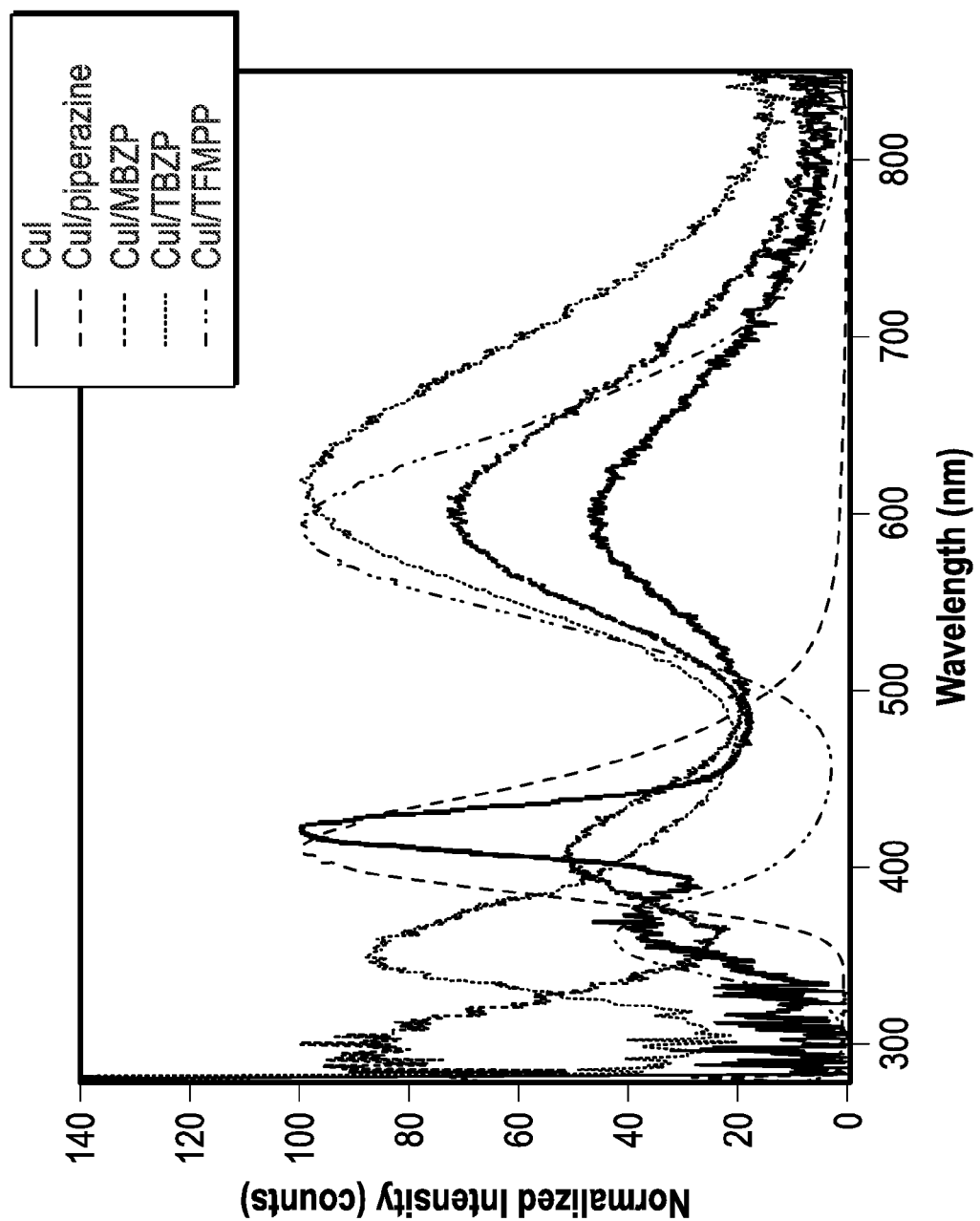
FIG. 7 is an exemplary graph of comparisons of resulting spectra of exemplary compounds in accordance with the present disclosure.

The resulting emission spectral data of a sample of an unknown substance on the test strip 104 can be used to presumptively identify substances of abuse. For example, FIG. 7 is a graph of the resulting spectra of some compounds—specifically, CuI-piperazine derivatives in FIG. 7. Note the characteristics of the emission peaks of the cluster compounds (CuI/substance) compared to the respective peaks of CuI and the substance. In the case of compounds with similar structures, such as piperazine and its derivatives as shown in FIG. 7, the cluster compounds formed with CuI luminesces at different wavelengths. This shows that these cluster compounds can result in spectral data that differs enough to be distinguished from one another, accounting for the minor change in chemical structure by displaying a large enough red or blue shift of similar peaks between compounds or different peaks all together.

Figure 8:
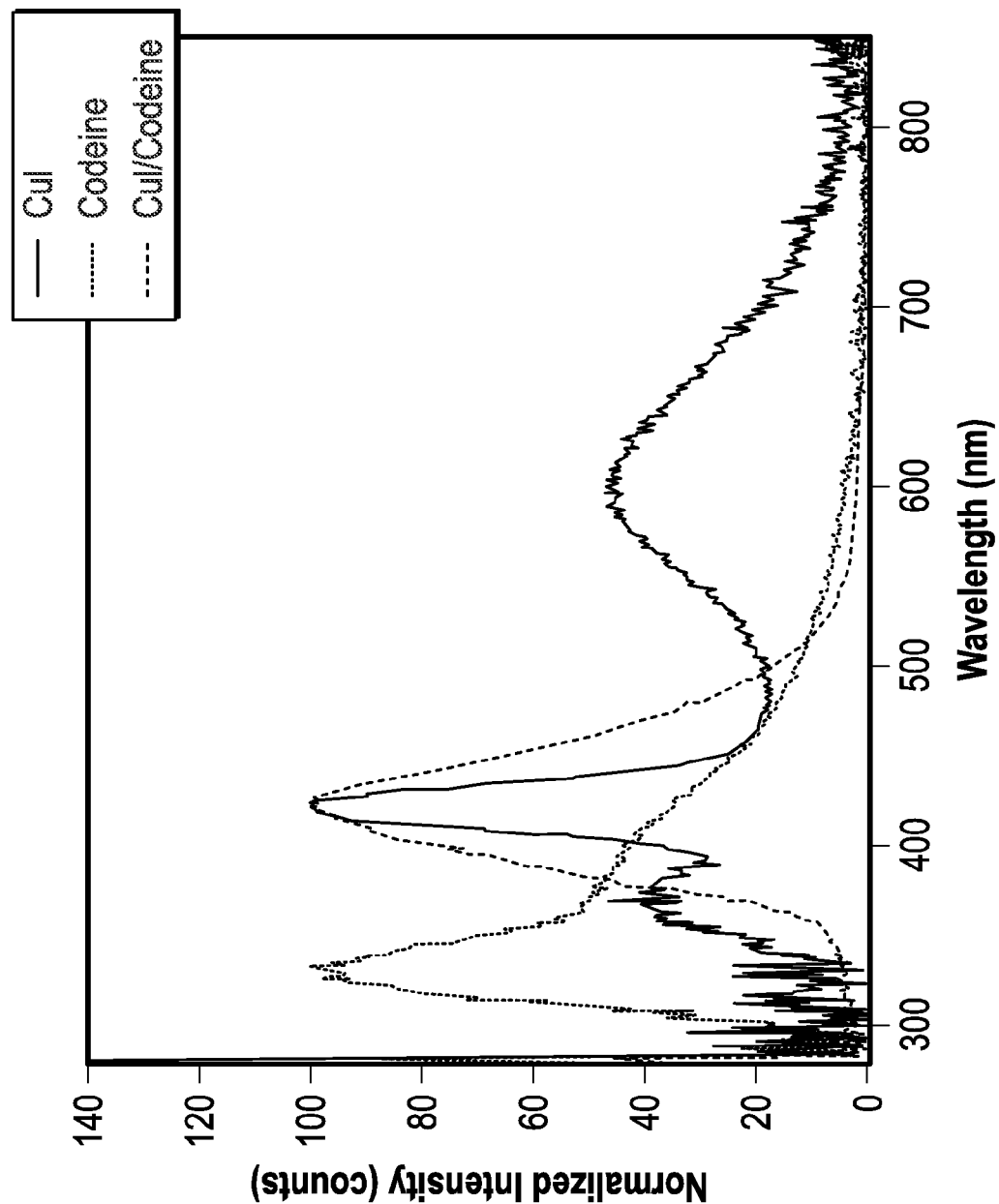
FIG. 8 is an exemplary graph of sample data from codeine (an opiate) on a test strip in accordance with the present disclosure.
Figure 9:
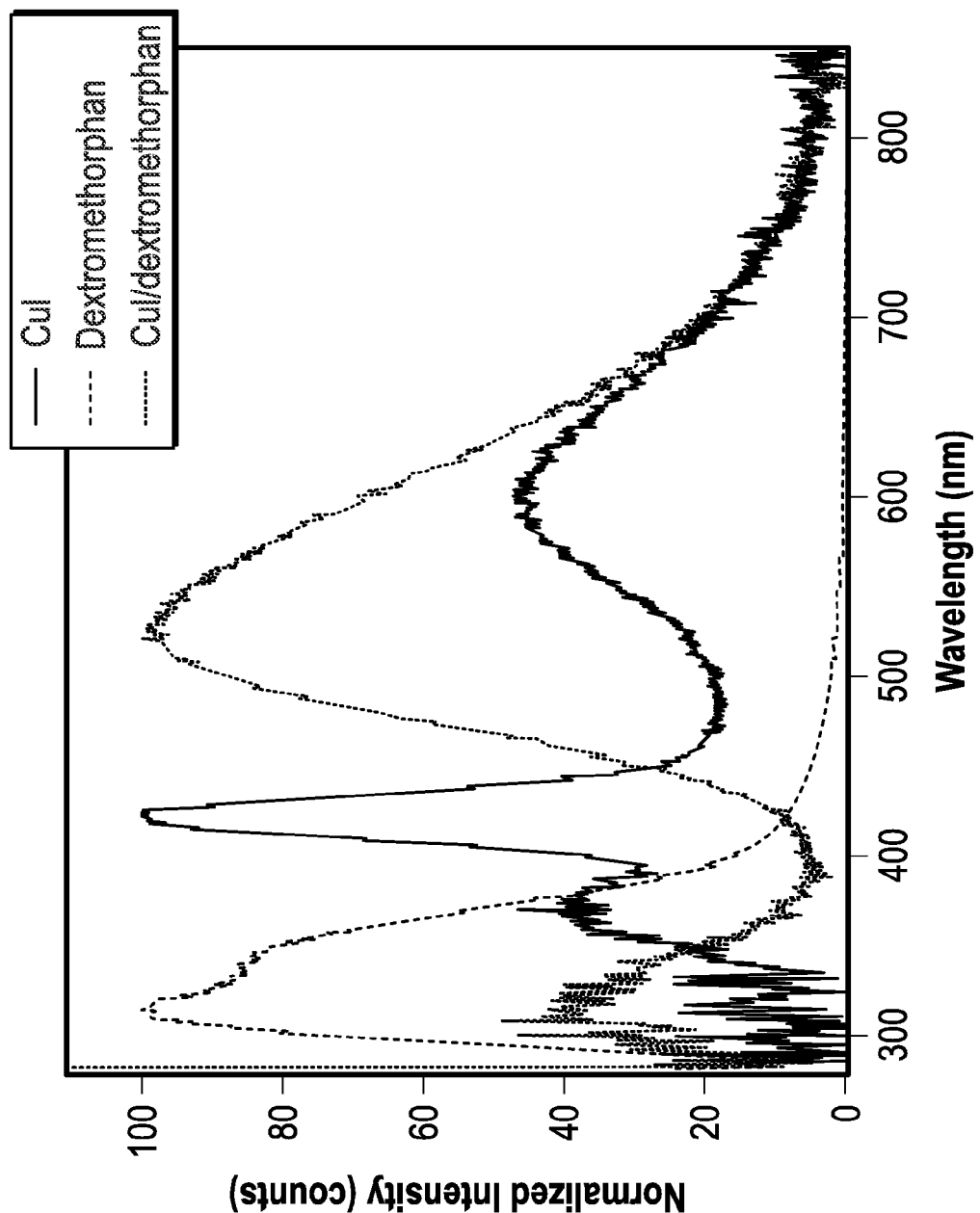
FIG. 9 is an exemplary graph of sample data from dextromethorphan (an alkaloid) on a test strip in accordance with the present disclosure.

Some substances of abuse were tested using the portable spectrometer system 10. For example, shown in FIGS. 8 and 9 are graphs of sample data for codeine (an opiate) and dextromethorphan (an alkaloid), respectively. Spectral data of medications and recreational drugs can be obtained over time to create a library database that can be used by officers and agents.

It should be understood that this approach is not limited to the identification of substances of abuse. It can also be used to identify the quality of petroleum products from new wells, the identity of biological stains (such as semen or urine), the identification of explosives, and any other application where a unique fluorescence signal can be measured.

CONCLUSION

The forensics community is in need of a more reliable and convenient test for on-site drug testing. Current methods such as Marquis' reagent and cobalt thiocyanate can yield many false positives and negatives and a portable GC-MS instrument requires proper training and is too expensive for every field officer or agent to have one. The portable spectrometer described herein is relatively inexpensive, easy to use, is compatible with smart phones, and yields more reliable results based on the luminescence spectra of $d^{10}$ metal cluster compounds with the drug itself as the ligands. Prior research has shown that the presently disclosed method of testing, especially when using copper(I) iodide, will yield a luminescent cluster compound with amines that emits in the visible spectrum range. The emission spectral profiles for each drug with different $d^{10}$ metal salts can be used to presumptively identify an unknown substance if it is an alkaloid, opiate, or some other amine compound.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. A portable spectrometer system, comprising:
   a test strip having a fluorescent indicator and adapted to receive a sample to be analyzed, wherein the test strip comprises a substrate at least partially coated with a $d^{10}$ metal salt; and further wherein the substrate is at least coated with a polymer selected from the group consisting of polyvinylpyrrolidone, polyvinyl alcohol, and combinations thereof;
   a fluorimeter comprising:
      a housing having a plurality of interconnected walls at least partially surrounding a cavity, at least one of the walls having an opening;
      a light source positioned in the cavity and adapted to emit light having a path;
      a support for receiving the test strip having the sample to be analyzed, the support located within the path of the light such that the light contacts the sample to cause an emission from the fluorescent indicator; and
      an optical spectrum separation assembly positioned to: receive the emission from the fluorescent indicator located at the support, separate the emission into an emission spectrum, and direct the separated emission spectrum through the opening;
   a mobile computing device comprising:
      an optical sensor positioned to receive the separated emission spectrum passing through the opening and to generate an image indicative of the separated emission spectrum; and
      a processor having instructions to analyze the image to determine the presence of and, if present, the identity of any illicit substance within the sample.

2. The portable spectrometer of claim 1, wherein the $d^{10}$ metal salt is a compound comprising a metal with an electronic configuration of $d^{10}$ and an anion selected from the group consisting of group 17 elements, cyanide (CN—), thiocyanate (SCN—), and combinations thereof.

3. The portable spectrometer system of claim 2, wherein the $d^{10}$ metal salt is selected from the group consisting of copper (I) iodide, copper (I) bromide, silver (I) iodide, silver (I) bromide, gold (I) bromide, gold (I) iodide, zinc iodide, zinc bromide, cadmium iodide, cadmium bromide, mercury (I) iodide, mercury (I) bromide, and combinations thereof.

4. The portable spectrometer system of claim 1, wherein the illicit substance to be analyzed comprises an amine group.

5. The portable spectrometer system of claim 1, wherein the at least one wall having the opening is a first wall, and wherein the fluorimeter further comprises a switch located on the first wall for sensing a presence of the mobile computing device on the first wall, the switch operably connected to the light source for enabling the light source to emit light responsive to the presence of the mobile computing device on the first wall.

6. The portable spectrometer system of claim 1, wherein the optical spectrum separation assembly comprises an optical guide within the cavity in the path of the light and constructed of a material that is opaque to the light, the optical guide having a slit in the path of the light that passes a portion of the light.

7. The portable spectrometer system of claim 1, wherein the processor has instructions to analyze the image to determine the identity of the illicit substance by comparing pixel values representative of emission spectra within the image to a library of emission spectra of known substances.

8. The portable spectrometer system of claim 1, wherein the mobile computing device is selected from the group consisting of a laptop computer, a cellular telephone, a personal digital assistant, a tablet computer, and combinations thereof, wherein the mobile computing device has at least one optical sensor.

9. The portable spectrometer system of claim 1, wherein the optical sensor is a camera.

10. The portable spectrometer system of claim 1, wherein the light source is a light emitting diode.

11. A method of analyzing a sample using the portable spectrometer system of claim 1, comprising the steps of:

contacting the test strip with a sample; and using the fluorimeter and mobile computing device to analyze for the presence of an illicit substance and, if present, identify the illicit substance within the sample.

12. The method of claim 11, wherein the step of contacting the test strip with the sample comprises:

contacting the sample on the test strip; and adding a solvent to the sample and the test strip.

13. The method of claim 12, wherein the solvent comprises a weakly coordinating nitrogen-containing solvent selected from the group consisting of amides, nitriles, and combinations thereof.

14. The method of claim 13, wherein the solvent comprises acetonitrile.

15. The method of claim 12, wherein the test strip contacted with the sample of the unknown sample is allowed to dry prior to the step of using the fluorimeter and mobile computing device.

16. The method of claim 11, wherein the step of contacting the test strip with the sample comprises coating the test strip in a saturated solution comprising the sample and a solvent.

17. The method of claim 16, wherein the solvent comprises a weakly coordinating nitrogen-containing solvent selected from the group consisting of amides, nitriles, and combinations thereof.

18. The method of claim 17, wherein the solvent comprises acetonitrile.

19. The method of claim 16, wherein the test strip contacted with the sample is allowed to dry prior to the step of using the fluorimeter and mobile computing device.

20. The method of claim 11, wherein the step of contacting the test strip with the sample produces a luminescent cluster compound in the area of contact between the sample and the test strip when the sample substance comprises an amine group.

21. The method of claim 20, wherein the luminescent cluster compound is stimulated by UV radiation in the step of using the fluorimeter and the mobile computing device.

22. The method of claim 11, wherein the illicit substance within the sample comprises at least one of an opiate and an alkaloid.

23. A test strip having a fluorescent indicator and adapted to receive a sample of an illicit substance to be analyzed, wherein the test strip comprises a substrate at least partially coated with:

(i) a solution of the illicit substance in a solvent: and (ii) the fluorescent indicator consisting of a $d^{10}$ metal salt and a polymer selected from the group consisting of polyvinylpyrrolidone, polyvinyl alcohol, and combinations thereof.

24. The test strip of claim 23, comprising a substrate, wherein the $d^{10}$ metal salt is coated by dipping the test strip into a solution of the $d^{10}$ metal salt and a nitrogen-containing solvent, and thereafter the $d^{10}$ metal salt coating has a thickness on the substrate in a range from about 1 pm to about 1 mm.

* * * * *

UNITED STATES PATENT AND TRADEMARK OFFICE
CERTIFICATE OF CORRECTION

PATENT NO. : 10,101,278 B2  
APPLICATION NO. : 14/889318  
DATED : October 16, 2018  
INVENTOR(S) : Richard George Blair Page 1 of 1

It is certified that error appears in the above-identified patent and that said Letters Patent is hereby corrected as shown below:

In the Specification  
Column 3, Line 44: Before "orbitals" insert -- 'd' --

Signed and Sealed this  
Eighth Day of January, 2019

Andrei Iancu  
*Director of the United States Patent and Trademark Office*